US010730009B2

United States Patent
Gerner et al.

(10) Patent No.: US 10,730,009 B2
(45) Date of Patent: Aug. 4, 2020

(54) METHOD FOR CLEANING THE EXHAUST AIR OF A GRANULATING SYSTEM FOR PRODUCING A UREA-CONTAINING GRANULATE

(71) Applicants: THYSSENKRUPP FERTILIZER TECHNOLOGY GMBH, Dortmund (DE); thyssenkrupp AG, Essen (DE)

(72) Inventors: Thomas Gerner, Dortmund (DE); Rositsa Marianova Rieks, Dortmund (DE)

(73) Assignees: THYSSENKRUPP FERTILIZER TECHNOLOGY GMBH, Dortmund (DE); THYSSENKRUPP AG, Essen (DE)

(*) Notice: Subject to any disclaimer, the term of this patent is extended or adjusted under 35 U.S.C. 154(b) by 0 days.

(21) Appl. No.: 16/489,136

(22) PCT Filed: Feb. 22, 2018

(86) PCT No.: PCT/EP2018/054331
§ 371 (c)(1),
(2) Date: Aug. 27, 2019

(87) PCT Pub. No.: WO2018/158126
PCT Pub. Date: Sep. 7, 2018

(65) Prior Publication Data
US 2019/0388835 A1 Dec. 26, 2019

(30) Foreign Application Priority Data
Feb. 28, 2017 (DE) .................. 10 2017 203 251

(51) Int. Cl.
*B01D 47/12* (2006.01)
*B01D 53/58* (2006.01)
*B01D 53/75* (2006.01)
*B01D 53/78* (2006.01)
*C07C 273/16* (2006.01)

(52) U.S. Cl.
CPC ............ *B01D 53/58* (2013.01); *B01D 47/12* (2013.01); *B01D 53/75* (2013.01); *B01D 53/78* (2013.01); *C07C 273/16* (2013.01)

(58) Field of Classification Search
CPC ... C07C 273/16; C07C 273/08; C07C 273/14; B01D 53/78; B01D 53/75; B01D 47/12; B01D 2251/504; B01D 53/58; B01D 2251/506; B01D 2257/406; B01J 10/00; B01J 2219/00002; B01J 2219/0004; B01J 2219/0059
See application file for complete search history.

(56) References Cited

U.S. PATENT DOCUMENTS

| 3,798,021 | A | 3/1974 | Bress | |
|---|---|---|---|---|
| 8,080,687 | B2 | 12/2011 | Niehues | |
| 10,500,535 | B2* | 12/2019 | Higgins | ............... B01D 47/12 |
| 2010/0296993 | A1* | 11/2010 | Hunsinger | ............ B01D 53/68 423/243.06 |
| 2019/0276392 | A1* | 9/2019 | Puci | ..................... B01D 53/002 |
| 2019/0359558 | A1* | 11/2019 | Rugnone | ............... B01D 3/009 |

FOREIGN PATENT DOCUMENTS

| EP | 0 514 902 A | 11/1992 | |
|---|---|---|---|
| EP | 2 192 099 A | 6/2010 | |
| EP | 2 477 961 B1 * | 4/2016 | ............... C01C 1/12 |
| EP | 3 016 731 B1 * | 1/2018 | ............. B01D 47/10 |
| EP | 3 517 505 A1 * | 7/2019 | ............... C02F 3/28 |
| FR | 1283156 A | 2/1962 | |
| JP | 2000-001466 A | 1/2000 | |
| RU | 2493903 C | 9/2013 | |
| WO | 2011032786 A | 3/2011 | |
| WO | 2012/034650 A | 3/2012 | |
| WO | 2014/094987 A | 6/2014 | |
| WO | 2016/074813 A | 5/2016 | |

OTHER PUBLICATIONS

English Translation of International Search Report issued in PCT/EP2018/054331, dated Jun. 4, 2018.

* cited by examiner

*Primary Examiner* — Timothy C Vanoy
(74) *Attorney, Agent, or Firm* — thyssenkrupp North America, LLC

(57) ABSTRACT

A process for purifying exhaust air from a granulation plant for producing a urea-containing granulate includes contacting a gas stream containing a urea-containing dust and ammonia with a sulfuric acid solution or a nitric acid solution in a scrubbing process. The scrubbing process involves scrubbing the gas stream with a first weakly acidic scrubbing solution in a first scrubbing stage and scrubbing the gas stream exiting the first scrubbing stage with a second scrubbing solution having a lower pH than the first weakly acidic scrubbing solution in a second scrubbing stage. The acidic scrubbing solution generated in the second scrubbing stage may be recycled into the first scrubbing stage via a conduit and used therein as the first weakly acidic scrubbing solution. A pre-scrubbing stage for scrubbing dust out of the gas stream may additionally be arranged upstream of the first scrubbing stage.

15 Claims, 1 Drawing Sheet

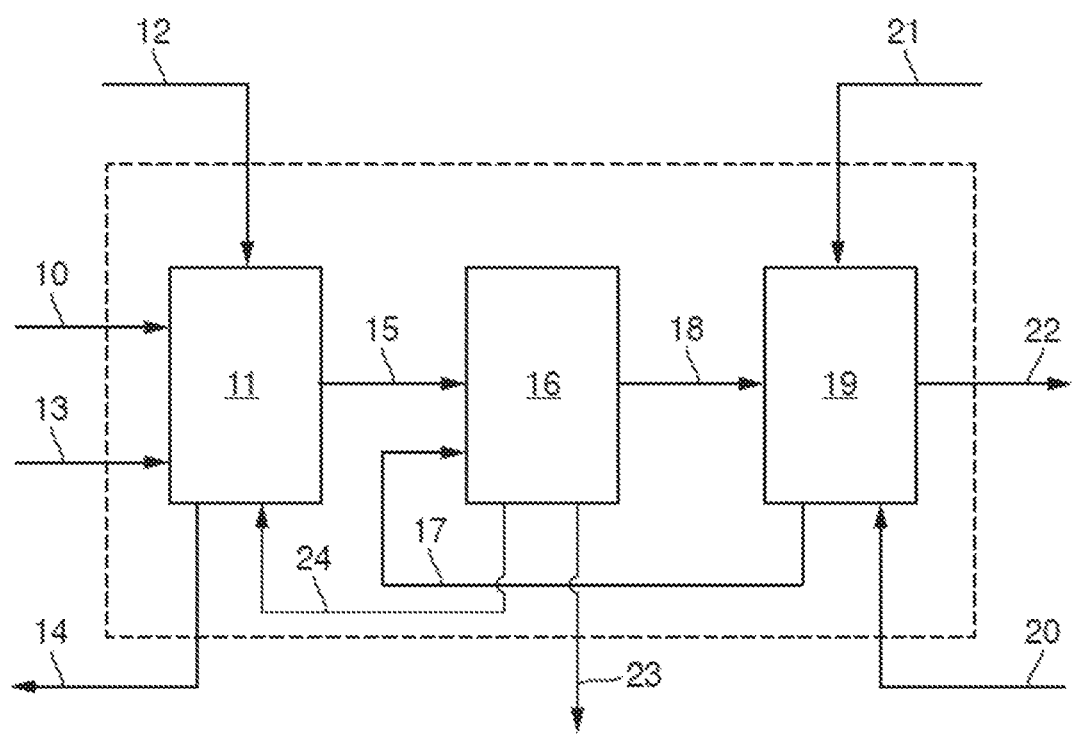

METHOD FOR CLEANING THE EXHAUST AIR OF A GRANULATING SYSTEM FOR PRODUCING A UREA-CONTAINING GRANULATE

CROSS REFERENCE TO RELATED APPLICATIONS

This application is a U.S. National Stage Entry of International Patent Application Serial Number PCT/EP2018/054331, filed Feb. 22, 2018, which claims priority to German Patent Application No. DE 10 2017 203 251.0, filed Feb. 28, 2017, the entire contents of both of which are incorporated herein by reference.

FIELD

The present disclosure generally relates to a process for purifying the exhaust air from a granulation plant.

BACKGROUND

The exhaust air from a granulation plant for producing a urea-containing granulate contains urea-containing dusts and ammonia and purifying of the exhaust air is therefore necessary before it can be discharged into the atmosphere. Known processes for exhaust air scrubbing in ammonia-containing gases generate an ammonium sulfate solution having a low pH (about pH 2-4) which cannot be directly subjected to further processing in this acidic form. An upward pH adjustment is therefore necessary to avoid corrosion damage in downstream process stages.

EP 2 477 961 B1 discloses a process for recovering urea dust and ammonia from a gas stream, wherein the gas stream is contacted with a sulfuric acid solution to form an acid solution of ammonium sulfate and urea, wherein this acid solution is admixed with ammonia. In this known process a gas stream containing air, urea and ammonia is contacted with an aqueous sulfuric acid solution in a scrubbing apparatus to form an acid solution of urea and ammonium sulfate. This acid solution is subsequently neutralized in a neutralization apparatus by addition of ammonia and then concentrated in a further apparatus. In a mixing apparatus the ratio of ammonium sulfate to urea may subsequently be increased to a desired value by addition of ammonium sulfate before the concentrated melt is finally processed into a solid by granulation or spray crystallization to obtain a solids mixture of urea and ammonium sulfate as the end product.

EP 2 192 099 A1 discloses a urea granulation process containing an acidic exhaust air treatment. The ammonium sulfate formed in the acidic exhaust air treatment may be returned into the granulation process.

WO 2016/074813 A1 discloses a urea granulation process comprising an exhaust air treatment comprising a dust scrubbing and an acidic exhaust air scrubbing.

Thus a need exists for a process for purifying the exhaust air from a granulation plant for producing a urea-containing granulate that dispenses with an external post-neutralization as a separate process step.

BRIEF DESCRIPTION OF THE FIGURE

FIG. 1 is a schematic view of an example installation for purifying exhaust air of a granulation plant for producing a urea-containing granulate.

DETAILED DESCRIPTION

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents. Moreover, those having ordinary skill in the art will understand that reciting "a" element or "an" element in the appended claims does not restrict those claims to articles, apparatuses, systems, methods, or the like having only one of that element, even where other elements in the same claim or different claims are preceded by "at least one" or similar language. Similarly, it should be understood that the steps of any method claims need not necessarily be performed in the order in which they are recited, unless so required by the context of the claims. In addition, all references to one skilled in the art shall be understood to refer to one having ordinary skill in the art.

The present disclosure generally relates to processes for purifying exhaust air from a granulation plant for producing a urea-containing granulate wherein a gas stream containing a urea-containing dust and ammonia contacts a sulfuric acid solution or nitric acid solution in a scrubbing process.

According to the invention it is provided that the scrubbing process comprises at least three separate sequential scrubbing stages, wherein the gas stream is scrubbed with a first weakly acidic scrubbing solution in a first scrubbing stage and the gas stream exiting the first scrubbing stage is scrubbed with a second scrubbing solution having a lower pH than the first weakly acidic scrubbing solution in a second scrubbing stage. The invention provides that a pre-scrubbing of the gas stream in a pre-scrubbing stage, which is there to substantially reduce the amount of dust present in the exhaust air stream, is arranged upstream of the first scrubbing stage. To this end the gas stream may preferably be scrubbed with a dilute urea-containing solution in the pre-scrubbing stage. This generates a solution comprising an elevated content of urea which may then in turn be concentrated by evaporation. The thus-recovered urea may be reemployed in the granulation for producing a urea-containing granulate. This pre-scrubbing has the advantage that there is already a markedly reduced dust content in the two acidic scrubbing stages which follow. The separation of dust scrubbing (pre-scrubbing stage) and actual acid scrubbing (first and second scrubbing stage) allows for recycling of the urea present in the gas stream into the granulator and a separate removal of the ammonium sulfate generated in the acid scrubbing (first and second scrubbing stage). The ammonium sulfate may preferably be integrated into the granulation process as described in WO2012/034650 A1, for example in [0018]-[0022] and [0036]-[0040].

In addition, urea liberates isocyanates and ammonia ($NH_3$) upon contact with acid-containing scrubbing solutions. In addition to their known toxic properties isocyanates exhibit a tendency for forming aerosols which may be scrubbed out only with great difficulty and complexity and are readily apparent in the exhaust air on account of their brownish coloring. Examples for the removal of aerosols may be found in WO2014/094987 A1. A further side reaction is the reaction of urea with sulfuric acid to afford mono- or diurea sulfate which are not readily recyclable into the materials cycle.

A preferred development of the inventive solution to the problem provides that an acidic scrubbing solution generated in the second scrubbing stage is recycled into the first scrubbing stage and is used therein as the first weakly acidic scrubbing solution. Herein, in particular the first scrubbing solution in the first scrubbing stage may be run in crosscurrent with the gas stream to be scrubbed. Thus in this preferred variant of the process according to the invention one important step for achieving a separate pH correction of the acidic scrubbing solution within the multi-stage system for scrubbing the exhaust air is the running in countercurrent of the acidic scrubbing from a second scrubbing apparatus to a first scrubbing apparatus.

The first scrubbing solution used in the first scrubbing stage is only weakly acidic and thus has a higher pH than the more strongly acidic second scrubbing solution used in the second scrubbing stage. For example the first weakly acidic scrubbing solution is a urea- and ammonium sulfate-containing or ammonium nitrate-containing solution having a pH in the range from about 3.5 to about 6.1, preferably having a pH in the range from about 4.3 to about 5.3.

It is preferable when the second scrubbing solution has a pH of less than about 2. For example concentrated sulfuric acid or concentrated nitric acid and condensate from the concentration apparatus for the generated urea-containing and ammonium sulfate-containing solutions may be supplied in order thus to produce the second scrubbing solution having a pH of preferably less than 2.0 with which the gas stream exiting the first scrubbing stage is scrubbed again in the second scrubbing stage.

It is preferable when the first scrubbing solution in the first scrubbing stage is run in crosscurrent with the gas stream to be scrubbed.

The solution generated in the scrubbing operation in the first scrubbing stage generally contains a certain content of ammonium sulfate or ammonium nitrate and traces of urea and is discharged from the first scrubbing stage preferably as a solution having a pH which is for instance neutral or slightly basic. The solution discharged from the first scrubbing stage after the scrubbing operation is thus preferably an ammonium sulfate-containing or ammonium nitrate-containing solution having a pH greater than 7. This neutral or approximately neutral pH of the ammonium sulfate solution or ammonium nitrate solution has the advantage that the solution is no longer corrosive and may be directly subjected to further processing, for example may be concentrated by evaporation of the water content. A post-neutralization outside the scrubbing system is no longer necessary.

The gas stream is preferably scrubbed with a dilute urea solution in the pre-scrubbing stage. This may preferably be recirculated in the pre-scrubbing stage and subsequently sent for concentration and recycling into the granulator.

In the process according to the invention suitable process management thus makes it possible to carry out the above-mentioned pH correction within the scrubbing system and to dispense with an external post-neutralization as a separate process step.

In a preferred development of the invention the more strongly acidic scrubbing solution used in the second scrubbing stage may be produced when the second scrubbing apparatus is supplied with concentrated sulfuric acid or concentrated nitric acid and also with a condensate from the concentration apparatus for the generated urea-containing and ammonium sulfate-containing or ammonium nitrate-containing solutions.

In a preferred development of the process according to the invention the neutralized ammonium sulfate solution or ammonium nitrate solution from the first scrubbing stage is passed into the third scrubbing stage (pre-scrubbing stage), thus allowing for further utilization of the ammonium sulfate solution produced.

In a further preferred embodiment of the process according to the invention the neutralized ammonium sulfate solution or ammonium nitrate solution from the first scrubbing stage is discharged and for example sent for separate use or disposal.

It is preferable when the second scrubbing stage is supplied with a condensate from a concentration apparatus for the generated urea-containing and ammonium sulfate-containing or ammonium nitrate-containing solutions. Condensate feeding allows for dilution and adjustment of the solution.

In a preferred development of the process according to the invention the pre-scrubbing stage is likewise supplied with a condensate from the concentration apparatus for the generated urea-containing and ammonium sulfate-containing or ammonium nitrate-containing solutions, wherein in this pre-scrubbing stage the urea-containing dust is preferably scrubbed out with a urea-containing solution. Condensate feeding allows for dilution of the solution. This pre-scrubbing increases the urea content of the solution since the scrubbing solution absorbs urea-containing dust from the exhaust air stream to be scrubbed.

The present invention further provides an installation for purifying the exhaust air from a granulation plant for producing a urea-containing granulate, in particular for use in a process of the type described hereinabove, which comprises at least a first scrubbing apparatus in which a gas stream containing a urea-containing dust and ammonia from the granulation plant for producing a urea-containing granulate is scrubbed using an acidic scrubbing solution and which further comprises at least a second scrubbing apparatus in operative connection with the first scrubbing apparatus in which a gas stream exiting the first scrubbing apparatus is scrubbed with a further acidic scrubbing solution having a lower pH than the first scrubbing solution. The inventive concept accordingly provides at least two sequential scrubbing operations in each case with acidic scrubbing solutions and in each case in separate scrubbing apparatuses, wherein scrubbing is effected initially with a weakly acidic first scrubbing solution and subsequently with a more strongly acidic second scrubbing solution. The invention provides that the installation comprises at least a third scrubbing apparatus which is arranged upstream of the first scrubbing apparatus in the flow path and in which a pre-scrubbing for scrubbing out dust from the gas stream takes place. This considerably reduces the amount of dust to be absorbed in the two acidic scrubbing stages arranged downstream.

It is particularly preferable when the installation according to the invention comprises at least one recycling conduit by means of which a weakly acidic solution generated in the second scrubbing apparatus is recyclable into the first scrubbing apparatus for use as the first acidic scrubbing solution. In this variant it is thus particularly advantageous when the weakly acidic scrubbing solution used in the first scrubbing apparatus is produced by the scrubbing operation in the second scrubbing apparatus and may then be recycled from the second scrubbing apparatus into the first scrubbing apparatus.

A further preferred development of the installation according to the invention for purifying the exhaust air from a granulation plant for producing a urea-containing granulate provides that said installation comprises an exhaust air conduit which proceeds from a granulation plant for producing a urea-containing granulate and leads into the third scrubbing apparatus, wherein it further comprises an outlet-side gas conduit exiting the third scrubbing apparatus for exhaust air purified in the third scrubbing apparatus which leads from the third scrubbing apparatus to the first scrubbing apparatus and wherein it further comprises an outlet-side gas conduit exiting the first scrubbing apparatus for exhaust air purified in the first scrubbing apparatus which leads from the first scrubbing apparatus to the second scrubbing apparatus.

A further preferred development of the installation according to the invention for purifying the exhaust air from a granulation plant for producing a urea-containing granulate comprises at least one recycling conduit for a urea-containing solution which proceeds from the third scrubbing apparatus and leads to a concentration apparatus in which this urea-containing solution is concentrated, wherein it further comprises means for recycling the thus-recovered urea into the granulation plant for producing a urea-containing granulate.

An exemplary embodiment of the present invention is more particularly elucidated hereinbelow with reference to FIG. 1. The diagram shows a simplified process scheme and only the plant parts relevant in the context of the present invention are shown. Via an inlet conduit 10 the to-be-purified exhaust air from a granulation plant for producing a urea-containing granulate arrives in a scrubbing apparatus 11 which serves as a pre-scrubbing to scrub out the predominant proportion of the urea-containing dust from the exhaust air stream. In the present application this pre-scrubbing is also referred to as third scrubbing apparatus 11. A condensate from the concentration apparatus for the generated urea-containing and ammonium sulfate-containing solutions may be supplied to the scrubbing apparatus 11 via a conduit 12. Employed as the scrubbing medium in this scrubbing apparatus 11 is a urea-containing solution supplied to the scrubbing apparatus via the inlet conduit 13. The scrubbing procedure generates a urea-enriched solution which may contain urea in a concentration of 45% for example and which is discharged from the scrubbing apparatus 11 via the outlet conduit 14 and supplied to a concentration apparatus in which the water present in the solution is largely evaporated in order that the highly concentrated urea-containing solution may subsequently be recycled into the granulation plant for producing a urea-containing granulate.

After the scrubbing procedure in the prescrubber 11 the gas stream largely freed of dust exits the scrubbing apparatus 11 via the gas conduit 15 and is then supplied to a scrubbing apparatus 16 in which the gas stream is scrubbed with a weakly acidic solution, wherein in the present application this scrubbing apparatus 16 is described as the first scrubbing apparatus. The weakly acidic scrubbing solution used in this first scrubbing apparatus which has a pH of 4.8 for example and which is essentially a weakly acidic aqueous solution of urea and ammonium sulfate or ammonium nitrate is supplied to the scrubbing apparatus 16 via the inlet conduit 17. In the scrubbing apparatus 16 the weakly acidic scrubbing solution is run in crosscurrent with the gas stream introduced via the conduit 15. As is apparent from FIG. 1 this inlet conduit 17 for supplying the scrubbing solution into the first scrubbing apparatus 16 is an outlet conduit from a second scrubbing apparatus 19 as elucidated hereinbelow.

The gas stream that has been scrubbed in the first scrubbing apparatus 16 exits this first scrubbing apparatus via the gas conduit 18 and is then introduced into the second scrubbing apparatus 19 in which the gas stream is scrubbed again, namely with an acidic scrubbing solution which is more strongly acidic than the weakly acidic scrubbing solution used in the first scrubbing apparatus 16. For this scrubbing operation in the second scrubbing apparatus 19 concentrated sulfuric acid or nitric acid is introduced into the second scrubbing apparatus 19 via an input conduit 20. A condensate from the process may also be supplied to the second scrubbing apparatus 19 via the input conduit 21. In the second scrubbing apparatus 19 the acidic scrubbing operation is carried out for example with a scrubbing solution having a pH in the range of about 1.5. After this rescrubbing in the second scrubbing apparatus 19 the purified exhaust air stream is discharged via the outlet conduit 22 and may in principle be released to the atmosphere since it is virtually dust free and virtually no longer contains any ammonia.

Since the gas stream introduced into this second scrubbing apparatus still contains ammonia this scrubbing operation of the gas stream in the second scrubbing apparatus 19 forms ammonium sulfate or ammonium nitrate by reaction with the sulfuric acid or nitric acid introduced via the conduit 20. Since a partial neutralization with the ammonia from the gas stream takes place in the second scrubbing apparatus the scrubbing operation produces a solution which contains ammonium sulfate or ammonium nitrate and residual urea and has a weakly acidic pH of for example 4.8. This weakly acidic urea/ammonium sulfate or urea/ammonium nitrate solution is then recycled via the outlet conduit 17 of the second scrubbing apparatus 19 into the first scrubbing apparatus 16 and used therein as a scrubbing solution which is run in crosscurrent with the gas stream introduced via the conduit 15 and effects gas scrubbing in the first scrubbing apparatus 16. The conduit 17 is thus simultaneously the inlet conduit for scrubbing solution in the first scrubbing apparatus 16 through which the gas stream flows first. A first gas scrubbing with a first weakly acidic solutions thus takes place in the first scrubbing apparatus 16 and subsequently a second gas scrubbing with a more strongly acidic scrubbing solution takes place in the second scrubbing apparatus 19.

Since a further neutralization process takes place therein through reaction of the weakly acidic scrubbing solution with ammonia present in the gas stream it is possible to discharge, from the first scrubbing apparatus 16 via the outlet conduit 23, a substantially neutralized aqueous solution which contains a proportion of dissolved ammonium sulfate or ammonium nitrate, contains residual urea and has a pH of greater than 7.

In a variant shown in the exemplary embodiment according to FIG. 1 of the invention the neutralized ammonium sulfate solution or ammonium nitrate solution may also for example be passed from the first scrubbing stage 16 into a third scrubbing stage (pre-scrubbing 11) via the conduit 24.

The setup according to the invention thus comprises three scrubbing stages for purifying the exhaust air released from the granulator of dust (pre-scrubbing stage) and two subsequent stages for removing ammonia and simultaneously raising the pH into a range less corrosive for the conduits in the first and second scrubbing stage.

LIST OF REFERENCE NUMERALS

10 Inlet conduit
11 Pre-scrubbing (third scrubbing apparatus)
12 Conduit for condensate
13 Inlet conduit for urea-containing scrubbing solution
14 Outlet conduit for urea-containing solution
15 Gas conduit
16 First scrubbing apparatus
17 Inlet conduit for scrubbing solution
18 Gas conduit
19 Second scrubbing apparatus
20 Inlet conduit for sulfuric acid or nitric acid 21 Inlet conduit for condensate
22 Outlet conduit for purified exhaust gas stream
23 Outlet conduit for neutralized ammonium sulfate solution or neutralized ammonium nitrate solution
24 Outlet conduit for neutralized ammonium sulfate solution or neutralized ammonium nitrate solution

What is claimed is:

1. A process for purifying exhaust air from a granulation plant for producing a urea-containing granulate, the process comprising:
  causing a gas stream containing a urea-containing dust and ammonia to contact a sulfuric acid solution or a nitric acid solution in a scrubbing process, wherein the scrubbing process comprises at least two separate sequential scrubbing stages including:
    pre-scrubbing dust out of the gas stream in a pre-scrubbing stage, scrubbing the gas stream with a first weakly acidic scrubbing solution in a first scrubbing stage downstream of the pre-scrubbing stage, and
    scrubbing the gas stream exiting the first scrubbing stage with a second scrubbing solution having a lower pH than the first weakly acidic scrubbing solution in a second scrubbing stage.

2. The process of claim 1 comprising recycling an acidic scrubbing solution generated in the second scrubbing stage into the first scrubbing stage as the first weakly acidic scrubbing solution.

3. The process of claim 1 wherein the first weakly acidic scrubbing solution is a urea- and ammonium sulfate-containing solution or an ammonium nitrate-containing solution having a pH in a range from 3.5 to 6.1.

4. The process of claim 1 wherein the second scrubbing solution has a pH of less than 2.

5. The process of claim 1 wherein the first scrubbing solution in the first scrubbing stage is run in crosscurrent with the gas stream to be scrubbed.

6. The process of claim 1 comprising discharging an ammonium sulfate-containing solution or an ammonium nitrate-containing solution having a pH of more than 7 from the first scrubbing stage.

7. The process of claim 1 comprising scrubbing the gas stream with a dilute urea solution in the pre-scrubbing stage.

8. The process of claim 1 comprising passing a neutralized ammonium sulfate solution or a neutralized ammonium nitrate solution from the first scrubbing stage into the pre-scrubbing stage.

9. The process of claim 1 comprising discharging a neutralized ammonium sulfate solution or a neutralized ammonium nitrate solution from the first scrubbing stage.

10. The process of claim 1 comprising supplying the second scrubbing stage with a condensate from a concentration apparatus for the urea-containing and ammonium sulfate-containing or ammonium nitrate-containing solutions.

11. The process of claim 1 comprising supplying the pre-scrubbing stage with a condensate from a concentration apparatus for the urea-containing and ammonium sulfate-containing solutions.

12. An installation for purifying exhaust air from a granulation plant for producing a urea-containing granulate, the installation comprising:
  a first scrubbing apparatus in which a gas stream containing a urea-containing dust and ammonia from the granulation plant is scrubbed using a first acidic scrubbing solution;
  a second scrubbing apparatus in operative connection with the first scrubbing apparatus in which a gas stream exiting the first scrubbing apparatus is scrubbed with a second acidic scrubbing solution having a lower pH than the first acidic scrubbing solution; and
  a third scrubbing apparatus disposed upstream of the first scrubbing apparatus in a flow path, wherein pre-scrubbing occurs in the third scrubbing apparatus for scrubbing out dust from the gas stream.

13. The installation of claim 12 comprising a recycling conduit by way of which a weakly acidic solution generated in the second scrubbing apparatus is configured to be recycled into the first scrubbing apparatus as the first acidic scrubbing solution.

14. The installation of claim 12 comprising:
  an exhaust air conduit that extends from the granulation plant into the third scrubbing apparatus;
  a first outlet-side gas conduit exiting the third scrubbing apparatus for exhaust air purified in the third scrubbing apparatus that leads from the third scrubbing apparatus to the first scrubbing apparatus; and
  a second outlet-side gas conduit exiting the first scrubbing apparatus for exhaust air purified in the first scrubbing apparatus that leads from the first scrubbing apparatus to the second scrubbing apparatus.

15. The installation of claim 12 comprising:
  a recycling conduit for a urea-containing solution that extends from the third scrubbing apparatus to a concentration apparatus in which the urea-containing solution is concentrated; and
  means for recycling recovered concentrated urea-containing solution into the granulation plant.

* * * * *